(12) United States Patent
He et al.

(10) Patent No.: US 8,975,453 B2
(45) Date of Patent: Mar. 10, 2015

(54) CATALYTIC CONVERSION OF GLYCEROL OR ACETOL TO ALCOHOLS

(71) Applicant: University of Idaho, Moscow, ID (US)

(72) Inventors: Bingjun Brian He, Moscow, ID (US); Randy Latayan Maglinao, Havre, MT (US)

(73) Assignee: University of Idaho, Moscow, ID (US)

( * ) Notice: Subject to any disclaimer, the term of this patent is extended or adjusted under 35 U.S.C. 154(b) by 115 days.

(21) Appl. No.: 13/792,965

(22) Filed: Mar. 11, 2013

(65) Prior Publication Data

US 2013/0245330 A1    Sep. 19, 2013

Related U.S. Application Data

(60) Provisional application No. 61/609,971, filed on Mar. 13, 2012.

(51) Int. Cl.
| | | |
|---|---|---|
| *C07C 29/149* | (2006.01) | |
| *C07C 29/145* | (2006.01) | |
| *C07C 29/143* | (2006.01) | |
| *C07C 29/60* | (2006.01) | |

(52) U.S. Cl.
CPC ............. *C07C 29/145* (2013.01); *C07C 29/149* (2013.01); *C07C 29/143* (2013.01); *C07C 29/60* (2013.01)
USPC .......................................... 568/885; 568/881

(58) Field of Classification Search
CPC .................................................... C07C 29/149
USPC ................................................. 568/885, 881
See application file for complete search history.

(56) References Cited

U.S. PATENT DOCUMENTS

| | | | |
|---|---|---|---|
| 7,790,937 B2 | 9/2010 | Henkelmann | |
| 7,812,200 B2 | 10/2010 | Franke | |
| 7,989,664 B2 | 8/2011 | Cortright | |
| 8,017,816 B2 | 9/2011 | Suppes | |
| 8,058,484 B2 | 11/2011 | Abhari | |
| 2011/0004029 A1 | 1/2011 | Chaudhari | |

OTHER PUBLICATIONS

Chiu, C-W, "Dehydration of Glyerol to Acetol via Catalytic Reactive Distillation," AIChE Journal, 52(10):3543-3548 (2006).
Dasari, Ma, "Low-Pressure Hydrogenolysis of Glycerol to Propylene Glycol," Applied Catalysis A General, 281:225-231 (2005).
Gandarias, I, "Hydrogenolysis of Glycerol to Propanediols over a Pt/ASA Catalyst: The Role of Acid and Metal Sites . . . ," Applied Catalysis B: Environmental, 97:248-256 (2010).
D'Hondt, E, "Catalytic Glycerol Conversion into 1,2-Propanediol in Absence of Added Hydrogen," Chem. Commun., 6011-6012 (2008).
Meryemoglu, B, "Aqueous Phase Reforming of Biomass Using Various Types of Supported Previous Metal and Raney-Nickel . . . ," Int. J. of Hydrogen Energy, 35:12580-12587 (2010).
Perosa, A, "Selective Hydrogenolysis of Glycerol with Raney Nickel," Ind. Eng. Chem. Res., 44:8835-8837 (2005).
Roy, D, "Aqueous Phase Hydrogenolysis of Glycerol to 1,2-propanediol Without External Hydrogen Addition," Catalysis Today, 156:31-37 (2010).
Smith, Ha, "The Role of Hydrogen in Raney Nickel Catalyst," J Phys. Chem., 59, 820-822 (1955).

*Primary Examiner* — Elvis O Price
(74) *Attorney, Agent, or Firm* — Howard Eisenberg, Esq.

(57) ABSTRACT

The catalytic conversion of glycerol or acetol to alcohols, such as polyhydric alcohols like propylene glycol and simple alcohols like methanol and ethanol, without the addition of external hydrogen, is improved by the use of a transition metal alloy catalyst which, in the case of glycerol, is a nickel alloy catalyst.

14 Claims, 2 Drawing Sheets

CATALYTIC CONVERSION OF GLYCEROL OR ACETOL TO ALCOHOLS

This application claims priority from pending U.S. Provisional Patent Application Ser. No. 61/609,971, filed on Mar. 13, 2012, which provisional application is incorporated into this application by reference in its entirety.

FIELD OF THE INVENTION

This application pertains to methods for catalytically converting glycerol and acetol to alcohols, such as polyhydric alcohols such as propylene glycol and simple alcohols such as methanol and ethanol.

BACKGROUND

The relevant prior art discloses the catalytic conversion of glycerol to alcohols by means of a catalytic thermochemical process without the need for an external supply of hydrogen. D'Hondt et al, Chem. Commun., 6011-6012 (2008), discloses the catalytic conversion of glycerol to propylene glycol in the absence of added hydrogen utilizing a platinum impregnated sodium/yttrium (NaY) zeolite catalyst. Utilizing this system, D'Hondt obtained a glycerol conversion rate of 85.4% and a yield of propylene glycol of 64% in 15 hours. The conversion rate and yield were reduced to 58.8% and 41.5%, respectively, if the reaction was run for only 4 hours. If the reaction was run for only 1 hour, the conversion rate and yield were reduced to only 18.1% and 25.0%, respectively.

Gandarias, Applied Catalysis B: Environmental, 97:248-256 (2010) likewise discloses the utilization of a platinum catalyst. The platinum catalyst of Gandarias was supported on an amorphous silica/alumina. Gandarias disclosed that, when exogenous hydrogen was added to the system, after a reaction time of 24 hours and at a pressure of 45 bar, a conversion rate of glycerol of about 20% was obtained with a yield of propylene glycol of about 32% (if the reaction was performed at 493° K) and a conversion rate of 90% with a yield of about 11.2% (if the reaction was performed at 513° K). However, in the absence of hydrogen, the conversion rate of glycerol after 24 hours was only 22.7% at 493° K and 34.8% at 513° K, and the yield of propylene glycol was 35.3% and 6.8%, respectively.

Roy, Catalysis Today, 156:31-37 (2010), discloses the catalytic conversion of a glycerol feedstock utilizing a reaction time of 6 hours and a catalyst made of an admixture of platinum and ruthenium. Conversion of glycerol at 493° K was reported to be about 50% with about 47% selectivity for propylene glycol. Conversion at 513° K was reported to be about 66%, but selectivity for propylene glycol was only about 30% at this higher temperature.

Similar results were disclosed in Chaudhari, U.S. Patent Application No. 2011/0004029. Utilizing either a platinum catalyst, a ruthenium catalyst, or a catalyst containing both platinum and ruthenium, glycerol was converted to various alcohols. As reported in Chaudhari, the conversion of glycerol by hydrogenolysis in the absence of external hydrogen with a 6-hour reaction time occurred with a temperature dependent conversion efficiency between 20.6% and 82.6%. At 473° K, conversion efficiency was 20.6% and selectivity for propylene glycol was 53.1%. However, as temperature was increased the conversion efficiency increased, to 82.6% at 523° K, but the selectivity of propylene glycol at this higher temperature was reduced to only 26.5%.

Smith, J. Phys. Chem., 59(9):820-822 (1955), discloses that a limited amount of hydrogen is associated with Raney nickel catalysts. Approximately one-half to one atom of hydrogen is present per atom of nickel in the catalyst. Smith discloses that, during a catalytic reaction, the hydrogen from the catalyst is removed and the activity of the catalyst is lost. Smith further discloses that the hydrogen lost during reaction is difficult to replace and that the activity of the Raney nickel catalyst therefore is reduced during a reaction as the hydrogen is removed from the catalyst.

Perosa, Ind. Eng. Chem. Res., 44:8535-8537 (2005), discloses the selective hydrogenolysis of glycerol to alcohols using a Raney® nickel (W.R. Grace & Co., Columbia, Md.) catalyst. Perosa discloses that a conversion rate of 12% with 93% selectivity was obtained after 20 hours with the addition of 10 atm of exogenous hydrogen gas. Perosa discloses that pressures of hydrogen below this level were insufficient to achieve significant conversion.

Each of the above cited references is incorporated herein by reference in their entirety.

Significant disadvantages are present with the above prior art methods for conversion of glycerol to alcohols. Most significant is that the reaction time required for the conversion of glycerol to alcohols, as disclosed in the prior art, is too long for the methods to be economically viable. A conversion of glycerol in a much shorter time span, such as two hours or less, would be desirable. Additionally, the conversion efficiency of glycerol and the selectivity for propylene glycol are low in the methods of the prior art. Therefore, it would be advantageous for a method to either increase the efficiency of glycerol or acetol conversion above that disclosed in the prior art or to increase the selectivity of this conversion to produce propylene glycol. It would further be advantageous for a method to both increase the efficiency of glycerol or acetol conversion and increase the selectivity of this conversion to propylene glycol.

DESCRIPTION OF THE INVENTION

Figure 1:
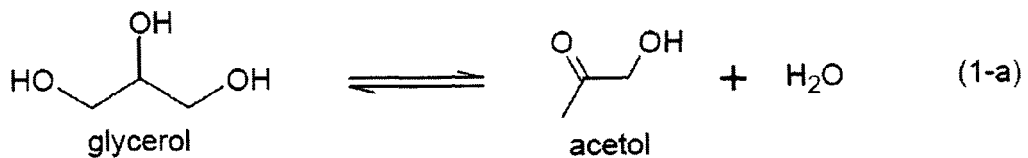
FIG. 1 is a series of chemical reaction schemes that may occur during the catalytic hydrogenolysis of glycerol and acetol to propylene glycol and other alcohols. Scheme 1 shows the conversion of glycerol to propylene glycol, with Scheme 1-a showing the conversion of glycerol to acetol and Scheme 1-b showing the subsequent conversion of acetol to propylene glycol. Scheme 2 shows the conversion of propylene glycol to ethanol. Scheme 3 shows the conversion of glycerol to ethylene glycol (Scheme 3-a) and of ethylene glycol to methanol (Scheme 3-b).
Figure 1:
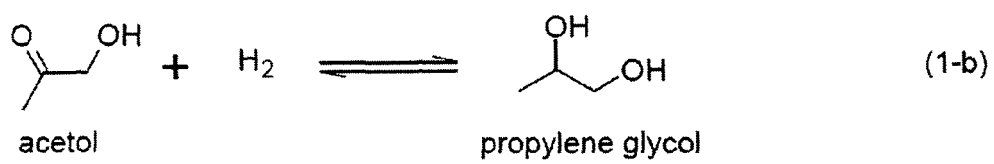
Figure 1:
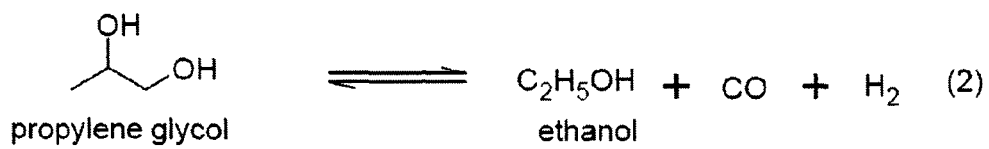
Figure 1:
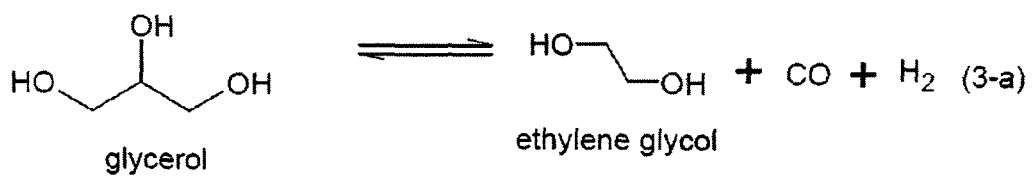
Figure 1:
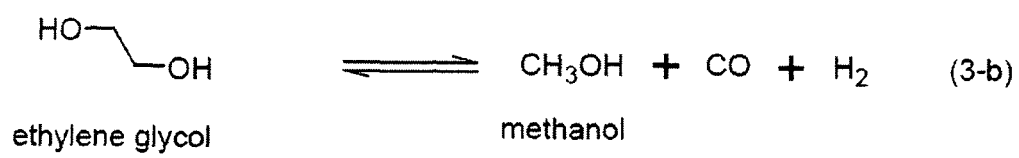

It has been unexpectedly discovered that the catalytic conversion of glycerol or acetol to alcohols, such as polyhydric alcohols like propylene glycol and simple alcohols like methanol, propanol, and ethanol, without the addition of external hydrogen or with only a low level of external hydrogen added, is improved by the use of a nickel alloy catalyst, such as a nickel aluminum alloy like a Raney nickel catalyst. It has been unexpectedly discovered that the necessary reaction time for the conversion of glycerol or acetol is greatly reduced by the use of this catalyst without external hydrogen. It has been further unexpectedly discovered that both the efficiency of conversion of glycerol or acetol and the selectivity of this conversion to propylene glycol is enhanced by the use of a nickel alloy catalyst in the absence of external hydrogen. Additionally, for the conversion of acetol, these unexpected advantageous results are obtained, not only with nickel alloy catalysts, but with other transition metal catalysts.

The discovery of the utility of a nickel alloy catalyst, such as a nickel aluminum alloy like Raney nickel, is especially unexpected in view of the teaching of the prior art of the requirement of an external source of hydrogen, at least 10 atmospheres if delivered as a gas, to obtain significant conversion of glycerol using a Raney nickel catalyst.

In this specification, the term "external hydrogen" refers to either elemental or molecular hydrogen or to a hydrocarbon source of hydrogen from outside sources during the catalytic conversion reaction. Specifically excluded from the term "external hydrogen" is hydrogen produced during the reaction from glycerol or acetol, from water, or from alcohols such as propylene glycol and simple alcohols like methanol and ethanol.

The term "feedstock" is defined as a raw material or mixture of raw materials supplied to a process from which other products can be made.

The term "conversion" is defined as the percentage of the substrate reacted to form products, and the term "yield" is defined as the amount of product obtained per unit weight or moles of raw material.

The term "hydrogenation" refers to a chemical reaction between molecular hydrogen and another compound or element.

The term "hydrogenolysis" refers to a chemical reaction in which one or more hydroxyl groups (—OH) in an organic compound is replaced by a hydrogen. The term hydrogenolysis may be used interchangeably with the term "hydrogenation," as hydrogenation may also occur during hydrogenolysis.

The term "reactor" refers to the part of a reaction vessel or system where substrates and chemical intermediates contact a catalyst to ultimately form products. The reactor for a simple reaction may be a single vessel containing a single catalyst. For a reaction requiring two different catalysts, the reactor may be a single vessel containing a mixture of the two catalysts, a single vessel such as tube reactor which contains two catalysts in two separate layers, or two vessels with a separate catalyst in each vessel, which catalysts may be the same or different in the two vessels.

According to the method of the present application, glycerol and/or acetol, a source of hydrogen other than external hydrogen, and a nickel alloy catalyst such as an nickel-aluminum alloy like Raney nickel in the case of glycerol, or a transition metal alloy catalyst such as nickel alloy such as a nickel-aluminum alloy like Raney nickel in the case of acetol, are combined, preferably within a reactor. Preferably, but not necessarily, oxygen is removed from the headspace within the reactor, such as by using nitrogen gas. The reactor is then heated to the desired temperature and maintained for a predetermined time. Upon completion of the reaction, if the temperature of the reactor during the reaction had been above room temperature, the reactor is preferably allowed to cool to room temperature. Any non-condensable gases, such as hydrogen, that formed during the reaction may be permitted to vent out and a liquid product containing one or more alcohols is obtained. Such venting is preferred if a batch process is desired. Alternatively, for example if a continuous flow process is desired, such gases may be recycled during or after the reaction.

Preferably, the reaction is performed in the absence of external hydrogen. Thus, any hydrogen that is required for hydrogenolysis or hydrogenation of glycerol or acetol is provided from a source other than a hydrocarbon or molecular or elemental hydrogen. Therefore, any hydrogen required for the reaction is produced from water or other external non-hydrocarbon source, or from the catalytic conversion of the glycerol or acetol. Besides water, other suitable non-hydrocarbon sources of hydrogen include organic alcohols.

Less preferably, the reaction is performed with the addition of exogenous hydrogen at a level below 10 atmospheres, if the exogenous hydrogen is in the form of a gas. Also, the reaction may be performed with the addition of exogenous hydrogen at a partial pressure of below 10 atmospheres, if the exogenous hydrogen is in a mixture of other gases, for example with nitrogen.

In the case of glycerol, the catalyst is an alloy of nickel. Examples of suitable nickel alloys include nickel-aluminum alloy, nickel-chromium-iron-aluminum alloy, iron-cobalt nickel ternary alloy, nickel-copper alloy, platinum nickel alloy on carbon, platinum nickel alloy on alumina, nickel-gold alloy, nickel-zinc alloy on alumina, and nickel-iron alloy. A preferred nickel alloy is a nickel-aluminum alloy such as a Raney nickel alloy.

The catalyst may include, in addition to the nickel alloy, a metal or an alloy of a metal other than an alloy of nickel. For example, the catalyst may contain, in addition to the nickel alloy, one or more transition metals, such as those listed in the next paragraph concerning the catalytic conversion of acetol. If the catalyst includes a metal other than a nickel alloy, it is preferred that the nickel alloy constitute at least 33% of the total transition metal in the catalyst used in the reaction process, more preferred that the nickel ally constitute at least 50% of the total transition metal in the catalyst, even more preferred that the nickel alloy constitute at least 66% of the catalyst, and most preferred that the nickel alloy constitute at least 75% of the catalyst.

When multiple catalysts are employed, the multiple catalysts may be unitary, meaning that the nickel alloy and the other metal are bound together. Alternatively, the multiple catalysts may be discrete, meaning that the nickel alloy and the other metal are not bound together.

For example, the catalyst may be in the form of a multi-layered catalyst bed, which bed contains a nickel alloy and a metal from any of the transition metals or transition metal oxides. Examples of such multi-layered catalyst systems include chromium on copper and a nickel alloy such as Raney nickel, or a heteropoly acid that contains a metal such as tungsten, molybdenum, or vanadium, and a nickel alloy, such as nickel on alumina or Raney nickel.

In the case of acetol, the catalyst is an alloy of one or more transition metals, a combination of an alloy of a transition metal with another metal such as a non-alloyed transition metal, or is a combination of more than one alloy of one or more transition metals. Transition metals suitable for the catalyst include scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, borhrium, hassium, meitnerium, ununnilium, unununium, and ununbium. Preferred transition metals suitable for the catalyst include scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, and mercury. Most preferred transition metals for the method of this application include iron, nickel, copper, and zinc. In a particularly preferred embodiment, the alloy is a nickel alloy such as a nickel-aluminum alloy like a Raney nickel catalyst.

In this specification, the term "alloy" refers to any metallic solid solution composed of two or more metal elements, and/or a homogeneous mixture of two or more metal elements at the molecular level. The alloy may include metals that are transition metals or that are other than transition metals.

In this specification, the term "promoter" refers to an element and/or compound, preferably metals, that are added to improve the activity or selectivity of the catalyst, but which themselves are not catalysts. Promoters are commonly but not always added as metallic ions to the catalyst. Promoters may be added to the catalyst by means that include washing the catalyst with a metallic ion solution, such as a zinc nitrate solution.

The catalyst may or may not be on a support, such as carbon, alumina, silica, zeolite, or other suitable material. The catalyst may or may not contain one or more promoters such as zinc, copper, or platinum.

The conversion of the glycerol or acetol in the presence of the source of hydrogen which is other than a hydrocarbon or elemental or molecular hydrogen, and which is preferably water, and in the presence of a catalyst as described above, preferably occurs within a reactor. Preferably, the headspace in the reactor is purged to remove oxygen. The purging may be by any suitable method, but is preferably performed by the use of nitrogen gas. The reactor is then heated to the desired temperature for the reaction, which may be from 0° C. or lower to about 600° C. or higher, but is preferably between 200° C. to 350° C., and most preferably between 220° C. to 320° C. The reactor is pressurized to the desired pressure, which may be from essentially 0 bars to 100 bars or higher. A preferred range of pressure is 0.5 to 65 bars and a most preferred range of pressures is from 1 to 50 bars. Upon completion of the reaction, the reactor is preferably allowed to cool to room temperature, if the reaction occurred at higher than room temperature, and preferably, any non-condensable gases in the reactor are removed. The liquid product of the reaction is collected from the reactor and may be separated from the catalyst by any suitable means, such as by using a vacuum filtration system.

In the case of acetol, the catalyst may be a catalyst as described above for glycerol or may be any catalyst that is known to catalyze the conversion of glycerol to alcohols, in the presence of or in the absence of external hydrogen. The catalyst for the conversion of acetol contains one or more transition metals and may or may not be an alloy. For example, the catalyst may be any of the catalysts disclosed in any of the D'Hondt, Gandarias, Roy, and Chaudhari references cited above and incorporated herein by reference.

In accordance with the method of this application, glycerol, crude glycerol, or acetol starting material is catalytically converted to high value alcohols such as propylene glycol, ethanol, and methanol with high product yield such as 50% or more in a much shorter time than previously reported. The method of this application achieves a complete conversion of the starting material within two hours. Because of this fast reaction rate, the production of propylene glycol and other alcohols from glycerol or acetol becomes economically viable with a greatly reduced capital cost from prior methods.

Additionally, the present method provides advantages including (1) the capability of performing the conversion process in a single reactor, (2) the utilization of water as a source of hydrogen for the reaction, (3) a very high conversion rate, up to 99.9% wt and high selectivity for propylene glycol if desired of 70% wt, (4) applicability of the method to either glycerol or acetol, with both starting materials providing high conversion and selectivity to propylene glycol, and (5) moderate operating conditions with a preferred range of temperature of 100° to 280° C., a preferred range of pressure of 1 to 50 bars, and a reaction time requiring only 5 to 120 minutes.

The catalyzed hydrogenolysis reactions of glycerol, and acetol, to alcohols such as propylene glycol, ethanol, and methanol are shown in FIG. 1. As shown in FIG. 1, glycerol is converted to acetol, which is then in turn converted to propylene glycol. Propylene glycol is also converted to ethanol. Additionally, glycerol is also directly converted to alcohols such as ethylene glycol and methanol.

A source of hydrogen is required for the method of this application. Unlike the prior art in which an exogenous source of hydrogen is utilized, the hydrogen that is utilized in the method of this application is obtained from aqueous starting material, glycerol or acetol, through the water-gas shift reaction.

Figure 2:
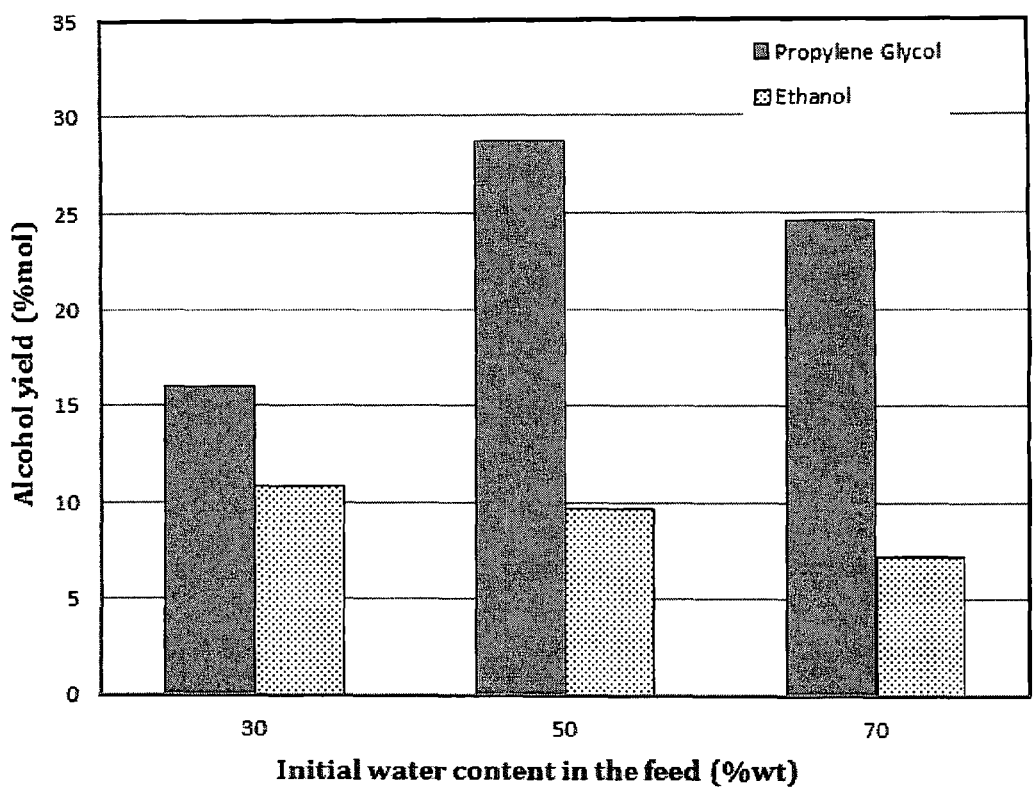
FIG. 2 is a bar graph that shows yields of alcohols obtained by the method of this application when utilizing different initial amounts of water in the feed relative to glycerol. Propylene glycol is indicated by the solid bars. Ethanol is indicated by the dotted bars.

By adjusting the mass ratio of water to glycerol or acetol in the feedstock, varying amounts of propylene glycol are produced. As shown in FIG. 2, a water concentration of 50 wt % resulted in the highest selectivity for propylene glycol. Ethanol selectivity was highest at lower concentrations of water.

The use of water as the source of hydrogen for the reaction provides several advantages. Besides being ubiquitous and inexpensive, the water inhibits undesirable side reactions such as degradation of the targeted products to undesirable products, as evidence by the absence of unwanted char and tar in the products of the reaction.

Because the method of this application does not require an external hydrogen supply, a one-unit operation may be utilized to provide a stepwise conversion of glycerol to acetol, and then to propylene glycol. For example, Scheme 1-a of FIG. 1 may be performed in the upper section of a unit operation, such as a tubular reactor, and in situ hydrogenation may be performed in the lower section of the unit using a different catalyst, if desired.

For many applications, a multi-layer catalyst bed is preferred because this arrangement permits specific reactions to occur in particular sections or locations within the reactor, rather than occurring randomly within the reactor along with other reactions. However, the configuration of the reactor is not limited to one or two layers. Rather, a multi-layered catalyst may be utilized to provide multiple discrete reaction steps.

For example for a three step conversion via Scheme 1-a of FIG. 1, the thermal decomposition of glycerol and acetol to hydrogen, and hydrogenation to propylene glycol, three layers of catalyst can be utilized. The process may also be configured, for example, using a two-stage reactor in series, such as two-tubular reactors in series or a tubular reactor and a continuous stirred tank reactor in series, wherein each reactor houses a different catalyst. Because exogenous hydrogen is not necessary in the process of this application, additional unit operations in between the two tubular reactors such as separation process and high pressure pumps can be eliminated, which reduces capital costs.

The invention is further described in the following non-limiting Examples which are illustrative of the invention.

EXAMPLE 1

General Procedure for Catalytic Conversion of Glycerol or Acetol

Reagent grade glycerol with 99.5% purity was utilized in the studies. Active Raney nickel catalyst was used. Acetol of higher than 95% purity was used.

A 300 ml pressure reactor was used for conducting the studies. Glycerol or acetol, water, and the catalyst were mixed in the reactor. Nitrogen gas was used to purge the headspace of the reactor for 1 minute to remove oxygen. The reactor was heated to 230° C. and maintained at that temperature during the reaction. Upon completion of the reaction, the reactor was cooled to room temperature and noncondensable gases that were formed during the reaction were removed through the exhaust valve and vented out. The final weight of the liquid product and catalyst was determined by measuring the reactor with the product (liquid and catalyst) and subtracting the premeasured weight of the empty reactor. The liquid product collected from the reactor was separated from the catalyst using a vacuum filtration at constant vacuum pressure of 16.9 kPa.

The amount of gas evolved during the reaction was estimated using the modified Benedict-Webb-Rubin gas equation for real gas mixtures. The difference in the pressure of the reactor before and after the reactor at the same temperature, specifically at 30° C., was assumed to represent the contribution of gas formed and was utilized in the gas equation.

EXAMPLE 2

Variation in Reaction Time

Glycerol was catalytically converted to propylene glycol and other alcohols by the process of Example 1 with varying times of reaction. The water to glycerol mass ratio in the feed for all data points was 1:1. The results are shown in Table 1.

TABLE 1

| Reaction Time (min) | Rate of Conversion (% mol) | Yields of Gases (% mol) |
| --- | --- | --- |
| 15 | 91.1 ± 2.3 | 13.1 ± 1.7 |
| 45 | 98.6 ± 0.2 | 18.2 ± 0.7 |
| 75 | 99.6 ± 0.5 | 30.9 ± 3.9 |
| 105 | 99.9 ± 0.1 | 33.9 ± 0.2 |

As shown in Table 1, more than 91% of the glycerol was converted with a reaction time of only 15 minutes, and more than 98% was converted after 45 minutes. The conversion rate was over 99% after 75 minutes.

EXAMPLE 3

Yield of Various Alcohols Versus Reaction Time

A gas chromatograph with a flame ionization detector was used for analyzing the primary and polyhydric alcohols and the residual glycerol produced by the reaction using the four reaction times of example 2.

For all time points, propylene glycol was the major reaction product. The yield of propylene glycol decreased linearly from 30.2% to 17.4% yield as the reaction time increased from 15 to 105 minutes. Conversely, the yield of ethanol increased linearly from 6.1% to 10.4% as the reaction time increased from 15 to 105 minutes. The yield of acetol was low for each reaction time and decreased from about 4% to 1% as the reaction time increased from 15 to 105 minutes. Other simple alcohols, such as methanol and 2-propanol, were also produced but in small amounts.

EXAMPLE 4

Variation in Ratio of Glycerol to Water

Glycerol was catalytically converted to propylene glycol and other alcohols by the process of Example 1 with a reaction time of 45 minutes and with variations in the ratios of water to glycerol. The results are shown in Table 2.

TABLE 2

| Water to Glycerol Mass Ratios | Rate of Conversion (% mol) | Yields of Gases (% mol) |
| --- | --- | --- |
| 7:3 | 99.9 ± 1.1 | 35.5 ± 2.8 |
| 1:1 | 98.6 ± 0.2 | 18.2 ± 0.7 |
| 3:7 | 95.3 ± 0.2 | 12.3 ± 0.3 |

The data of Table 2 show that the conversion of glycerol to alcohols is substantially complete at 45 minutes irrespective of the ratio of water to glycerol and that somewhat higher rates of conversion were obtained with higher ratios of water to glycerol.

EXAMPLE 5

Yield of Various Alcohols with Variation in Initial Water Content

The analysis of Example 3 was performed on the reaction products of the reactions of Example 4 to determine the yield of various alcohols with changes in initial ratio of water and glycerol. The results are shown graphically in FIG. 2.

As shown in FIG. 2, ethanol yield increased as the water content in the reaction solution increased. A similar trend was observed for gases that were produced in small amounts, such as methanol (not shown in FIG. 2). Conversely, a decrease in propylene glycol production occurred at higher water to glycerol mass ratios with a peak propylene glycol production occurring at a mass ratio of 1:1.

EXAMPLE 6

Variation in Amount of Catalyst Used

Glycerol was catalytically converted to propylene glycol and other alcohols by the process of Example 1 with a reaction time of 45 minutes, a water:glycerol ratio of 1:1, and with variations in the amount of catalyst used. The concentration wt % of catalyst was varied from 1.0% to 8.9%.

Increasing the concentration of catalyst from provided an increase in ethanol production from about 1% yield to about 9% yield. The increase in ethanol production appeared to be linear until a catalyst concentration of 6.4% was used. A further increase in concentration of catalyst to 8.9% produced a further increase in ethanol production but the slope of the increase in ethanol production decreased between these two points when compared to the lower catalyst concentration points. The yield of propylene glycol followed a quadratic path and greatly increased from about 4% to 32% as the concentration of catalyst increased from 1.0% to 6.4%. Increasing the concentration of catalyst to 8.9%, however, resulted in a decrease in propylene glycol yield to about 30%.

The decrease in yield of propylene glycol and the slowing of the increase in yield of ethanol when increasing the concentration of catalyst from 6.4% to 8.9% suggests that increasing the concentration of catalyst above 6.4% does not significantly improve the yields of these two alcohols under the conditions that were studied. However, the overall conversion of glycerol and yields of alcohols were greatly affected by changes in dosage of catalyst. As shown in Table 3, glycerol conversion increased from 49.04 to 98.59 mol % and the gas yields increased from 3.69 to 17.60 mol % when increased concentrations of catalyst, from 1.0 wt % to 8.9 wt %, were utilized.

TABLE 3

| Catalyst Concentration (wt %) | Glycerol Conversion Rate (mol %) | Yield of Gas (mol %) |
|---|---|---|
| 1.0 | 49.04 | 3.69 |
| 2.9 | 77.19 | 8.31 |
| 4.7 | 87.95 | 12.12 |
| 6.4 | 95.75 | 16.36 |
| 8.9 | 98.59 | 17.60 |

EXAMPLE 7

Acetol Feedstock

The procedure of Example 1 was repeated but using acetol as the feedstock in place of glycerol. 100 g of an acetol/water mixture with a 5:1 water to acetol molar ratio and 9.1 wt % Raney nickel catalyst concentration were utilized. The reaction was performed in a time of 20 minutes and in a time of 65 minutes. The results are shown below in Table 4.

TABLE 4

| | Reaction Time | |
|---|---|---|
| | 20 min | 65 min |
| Products | | |
| Propylene Glycol | 20.81 ± 2.44 | 17.11 ± 1.03 |
| Methanol | 0.71 ± 0.15 | 0.96 ± 0.12 |
| Ethanol | 5.18 ± 0.77 | 6.80 ± 0.26 |
| n-Propanol | 0.14 ± 0.12 | 0.25 ± 0.22 |
| Isopropanol | 0.02 ± 0.03 | 0.12 ± 0.03 |
| Gases | 12.52 ± 1.37 | 20.52 ± 0.54 |
| Acetol Conversion rate (% mol) | 98.55 ± 1.89 | 98.59 ± 1.56 |

As shown in Table 4, acetol was converted in a hydrogenation reaction without the addition of external hydrogen in a time of 20 minutes. When the reaction was allowed to continue beyond this time, the yield of propylene glycol dropped and the yield of other alcohols, such as ethanol, methanol, n-propanol, and isopropanol, increased.

EXAMPLE 8

Conversion of Acetol Using Different Catalysts

The procedure of Example 7 is repeated utilizing catalysts other than those containing a nickel alloy. The procedure of Example 7 is repeated utilizing a ruthenium on alumina catalyst, a platinum oxide catalyst, and a rhenium oxide on alumina catalyst. Acetol is converted without the addition of external hydrogen in a time of 20 minutes.

While preferred embodiments of the invention have been described in detail, it will be apparent to those skilled in the art that the disclosed embodiments may be modified. It is intended that such modifications be encompassed in the invention. Therefore, the foregoing description is to be considered to be exemplary rather than limiting, and the scope of the invention is that defined by the following claims.

The invention claimed is:

1. A method for catalytically converting glycerol to one or more alcohols, including propylene glycol, comprising combining in a suitable reactor, glycerol, a source of hydrogen other than a hydrocarbon or molecular hydrogen, and a nickel alloy catalyst, and allowing the glycerol to be converted to one or more alcohols, wherein the pressure of hydrogen gas within the reactor during the conversion is less than 10 atm, and wherein hydrogen required for the conversion is produced from water or from water and a non-hydrocarbon source other than water.

2. The method of claim 1 wherein the source of hydrogen is water or an alcohol.

3. The method of claim 1 wherein the nickel alloy is a nickel aluminum alloy.

4. The method of claim 3 wherein the nickel aluminum alloy is Raney® nickel.

5. The method of claim 1 wherein the catalyst is on a support.

6. A method for catalytically converting acetol to one or more alcohols, including propylene glycol, comprising combining in a suitable reactor, acetol, a source of hydrogen other than a hydrocarbon or molecular hydrogen, and a catalyst that contains a transition metal or an alloy of a transition metal, and allowing the acetol to be converted to one or more alcohols, wherein the pressure of hydrogen gas within the reactor during the conversion is less than 10 atm, and wherein hydrogen required for the conversion is produced from water or from water and a non-hydrocarbon source other than water.

7. The method of claim 6 wherein the source of hydrogen is water or an alcohol.

8. The method of claim 6 wherein the transition metal is selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, borhrium, hassium, meitnerium, ununnilium, unununium, and ununbium.

9. The method of claim 8 wherein the catalyst contains an alloy of a transition metal.

10. The method of claim 9 wherein the catalyst is a nickel alloy.

11. The method of claim 10 wherein the nickel alloy is a nickel aluminum alloy.

12. The method of claim 11 wherein the nickel aluminum alloy is Raney® nickel.

13. The method of claim 1 wherein the pressure of hydrogen gas within the reactor is 0 atm.

14. The method of claim 6 wherein the pressure of hydrogen gas within the reactor is 0 atm.

* * * * *